United States Patent [19]

Cosentino et al.

[11] Patent Number: 4,664,891
[45] Date of Patent: May 12, 1987

[54] DIALYSIS SOLUTION PREPARATION FROM PREPACKAGED DRY CHEMICALS

[75] Inventors: Louis C. Cosentino, Wayzata; Wayne I. Nelson, Brooklyn Park, both of Minn.

[73] Assignee: Renal Systems, Inc., Minneapolis, Minn.

[21] Appl. No.: 850,849

[22] Filed: Apr. 11, 1986

Related U.S. Application Data

[63] Continuation of Ser. No. 633,583, Jul. 23, 1984, abandoned.

[51] Int. Cl.⁴ .................. B01F 1/00; B01F 5/10; B65D 85/00
[52] U.S. Cl. .................... 422/269; 422/279; 422/281; 422/283; 206/524.1; 366/159; 366/169; 137/268
[58] Field of Search .............. 422/201, 269, 278, 279, 422/281, 283, 902; 210/96.2, 321.2; 366/159, 169; 252/176; 206/524.1, 524.4, 524.5; 137/268

[56] References Cited

U.S. PATENT DOCUMENTS

| | | | |
|---|---|---|---|
| 2,682,465 | 6/1954 | Wiitala et al. | 206/524.4 X |
| 3,352,779 | 11/1967 | Austin et al. | 210/96.2 X |
| 3,356,460 | 12/1967 | King et al. | 422/278 X |
| 4,265,760 | 5/1981 | Abel et al. | 210/321.2 X |
| 4,326,955 | 4/1982 | Babb et al. | 210/638 |
| 4,386,634 | 6/1983 | Stasz et al. | 141/2 |
| 4,489,535 | 12/1984 | Veltman | 206/524.1 X |

FOREIGN PATENT DOCUMENTS

| | | | |
|---|---|---|---|
| 699304 | 12/1964 | Canada | 366/169 |
| 456996 | 11/1936 | United Kingdom | 252/176 |

Primary Examiner—S. Leon Bashore
Assistant Examiner—Andrew J. Anderson
Attorney, Agent, or Firm—Vidas & Arrett

[57] ABSTRACT

A system and process for preparation of dialysis concentrate solution from dry chemicals and water. The source of hemodialysis chemicals for a batch is a drum selectively filled with dry chemicals such that an inner core region therewithin is loaded with chemicals which slurry and dissolve the least readily. The required amount of water is metered into a mix tank. Water is pumped from the tank into a spray head fitted over the selectively filled drum. Water is injected onto the chemicals within the inner core region by the use of a nozzle having a narrow spray angle. The chemicals within the inner core region are preferentially dissolved or slurried before the other chemicals within the drum. The slurried and dissolved chemicals are removed from the drum by a suction wand and are entirely solubilized in the tank. Cycling of fluid continues from the drum to the tank and vice versa until all of the chemicals in the drum have been removed. Circulation of the fluid is continued until a uniform solution results. The dialysis concentrate solution is filtered and checked for conductivity prior to dilution in a conventional proportioning system for ultimate use in hemodialysis.

13 Claims, 3 Drawing Figures

DIALYSIS SOLUTION PREPARATION FROM PREPACKAGED DRY CHEMICALS

This is a continuation of application Ser. No. 633,583, filed 7/23/84, now abandoned.

DESCRIPTION

1. Field of the Invention

This invention relates to the preparation of hemodialysis concentrate solution from its bulk constituents of water and dry chemicals. More particularly, it involves the arrangement of the dry chemicals within a container such that the chemicals which slurry and dissolve most slowly will tend to be placed into solution or otherwise removed from the container prior to the other chemicals through the use of the apparatus of invention.

2. Background of the Invention

Dialysis fluids for hemodialyzers are often formulated from a mixture of a concentrated solution of dialysis chemicals and purified water in a ratio of approximately one part of concentrate to 34 parts water by volume. Proportioning devices are utilized to maintain this user concentration within prescribed limits for the duration of the hemodialysis treatment which is often from 4 to 14 hours. Proportioning means in such delivery systems frequently are positive displacement mechanical devices, such as pistons or rotary pumps.

It is possible to prepare dialysis solution directly from dry reagents. This is unusual, however, since such preparation requires careful weighing of a number of ingredients, typically including sodium chloride, sodium bicarbonate or sodium acetate, potassium chloride, calcium chloride, magnesium chloride, lactic acid and dextrose. Merely 'dumping' these materials into water is less than satisfactory because of extreme slowness of total solution from such a mass. Because of this complexity, most dialysis solutions are prepared by dilution of commercially supplied concentrate.

Because of the added costs of shipping concentrate (shipping large amounts of water and container costs for liquid proof containers that will not be prone to breakages in shipping) it would be desirable to start from the dry chemicals at the point of use of the dialysis solution. For example, for larger institutions to prepare their own dialysis concentrate solutions it is economic to use drums of dry chemicals and use their own water supply to mix and create a concentrate.

In U.S. patent application Ser. No. 577,387 to William H. Harm et al filed Feb. 6, 1984, the disclosure of which is incorporated herein by reference, a dialysis concentrate solution mixing system is disclosed which prepares hemodialysis solution from two drums contining dry chemicals. The Harm et al system involves a spray head device which is fitted over the top of a drum filled with dry chemicals. Solubilizing water rains down upon the chemicals therebelow to form a slurry and to solubilize the same. A suction pick-up wand carries the slurry and dissolved chemicals into a larger mixing tank.

BRIEF SUMMARY OF THE INVENTION

The present invention relates to a system and method for preparing dialysis solution from water and shipping drums containing the dry chemicals. The dry chemicals are arranged therewithin to maximize transfer and dissolution while minimizing the time required to dissolve al the required chemicals.

The most commonly used chemicals in hemodialysis are sodium chlroide, sodium acetate, sodium bicarbonate, calcium chloride, dextrose, magnesium chloride and potassium chloride. In order to prevent possible operator error and to provide a simple, easy to operate system, all of these or additional dry chemicals are preferably contained in a single drum. However, it has been found that although all the chemicals are soluble in water, individually they have different solubility and transfer characteristics. Transfer of the dry chemicals from a drum to the mix tank using the general procedure of Harms et al, supra, involves both solubility and slurrying characteristics of individual dry chemicals. The different "transfer characteristics" of the chemicals greatly prolongs the time required to transfer a mixture of chemicals from a drum to a mix tank.

The system of the invention involves the prepacking of drums of dry hemodialysis chemicals wherein the chemical which dissolves or is dispersed the least readily and most slowly within water is packed within a central, generally cylindrical core within the drum. The other dry chemicals are packed around the core along the sides, the bottom and/or on top as desired. The drum is shipped in this condition for ultimate use.

The user system operates as follows. A spray plate is positioned over the top of an open, filled drum of dry chemicals so as to provide a liquid spray barrier. A spray nozzle perforates and extends from the spray plate and is supplied with water from a main mixing container. The nozzle preferably projects a full cone spray pattern over a relatively narrow spray angle to provide a high impact, relatively coarse spray which will directly impact the inner core region of dry chemicals having the least favorable solubility and transfer characteristics.

The injection of a high velocity spray of water over a narrow angle onto the sodium acetate selectively allows the sodium acetate to be solubilized and slurried ahead of significant quantities of the other dry chemicals. A suction pick-up wand, powered by a jet pump, extends through the spray plate and picks up the slurried chemicals. The pick up wand is gravity controlled and continues to descend into the drum once space is available.

As the process proceeds, a cone shaped cavity is formed within the sodium acetate causing any remaining sodium acetate to cave inwardly so as to form part of the water slurry. The generally cylindrical inner core region containing sodium acetate is thereby contacted by diluent before the other chemicals are dissolved in large amounts. Eventually, the majority of the sodium acetate has been solubilized or removed in a slurry. This occurs to a large degree prior to the time of solubilizing the other major constituents of the hemodialysis solution. The sodium acetate goes into slurry and solution much more rapidly due to the direct mechanical action. Once the sodium acetate has been largely removed from the drum the remaining soluble chemicals become slurried and solubilized within the drum. The suction wand continues to remove material from the drum until it is emptied of chemicals.

The slurried and solubilized chemicals within the main mixing tank continue to mix by connecting the suction line of the pick up wand to a suction tube extending through an opening into the mixing tank. Additional mixing within the mixing tank is provided by air induced into the tank through the suction line. Alternatively, a valve may be utilized to shift suction from the pick-up wand to the tank suction tube. After thoroughly being mixed, the dialysis concentrate solution is passed through a series of filters prior to use as a concentrate in a proportioning mixing system.

Alternatively, the solution may be prepared for direct hemodialysis use without needing further dilution. A series of pressure sensors, level sensor and valves may be employed in the system along with a master control to automate, to a major degree, the entire system.

It has been found that the unique prepackaging of the dry chemicals of the invention allows the preparation of large quantities of dialysis concentrate solution having a uniform chemical concentration in up to less than one-third of the time required by previous systems.

The invention provides many advantages. All of the required chemicals to make a batch may be shipped in a single, prepackaged drum. Since no water is shipped, shipping costs and handling problems are lessened. Quality control may be optimized since only water needs to be metered into a mix tank rather than a plurality of separate chemicals. Drums of dry chemicals are utilized having a fraction of the shipping weight of prior systems.

A single prepackaged drum containing all of the hemodialysis chemicals required to make one batch of solution desirably is utilized to prevent possible errors due to weighing, mixing and the like. Troublesome hemodialysis chemicals such as sodium acetate are readily and quickly slurried and solubilized due to their arrangement within an inner core region of the drum where they may be impacted upon by the narrow spray jet of water from the spray head system of the apparatus. As a result, the time required to slurry, solubilize and transfer a container of dry chemicals to a mix tank may be reduced by as much as two-thirds by the devices and processes of the invention.

BRIEF DESCRIPTION OF THE DRAWINGS

A detailed description of one preferred embodiment of my invention is hereafter described with specific reference being made to the drawings in which.

DETAILED DESCRIPTION OF THE INVENTION

Figure 1:
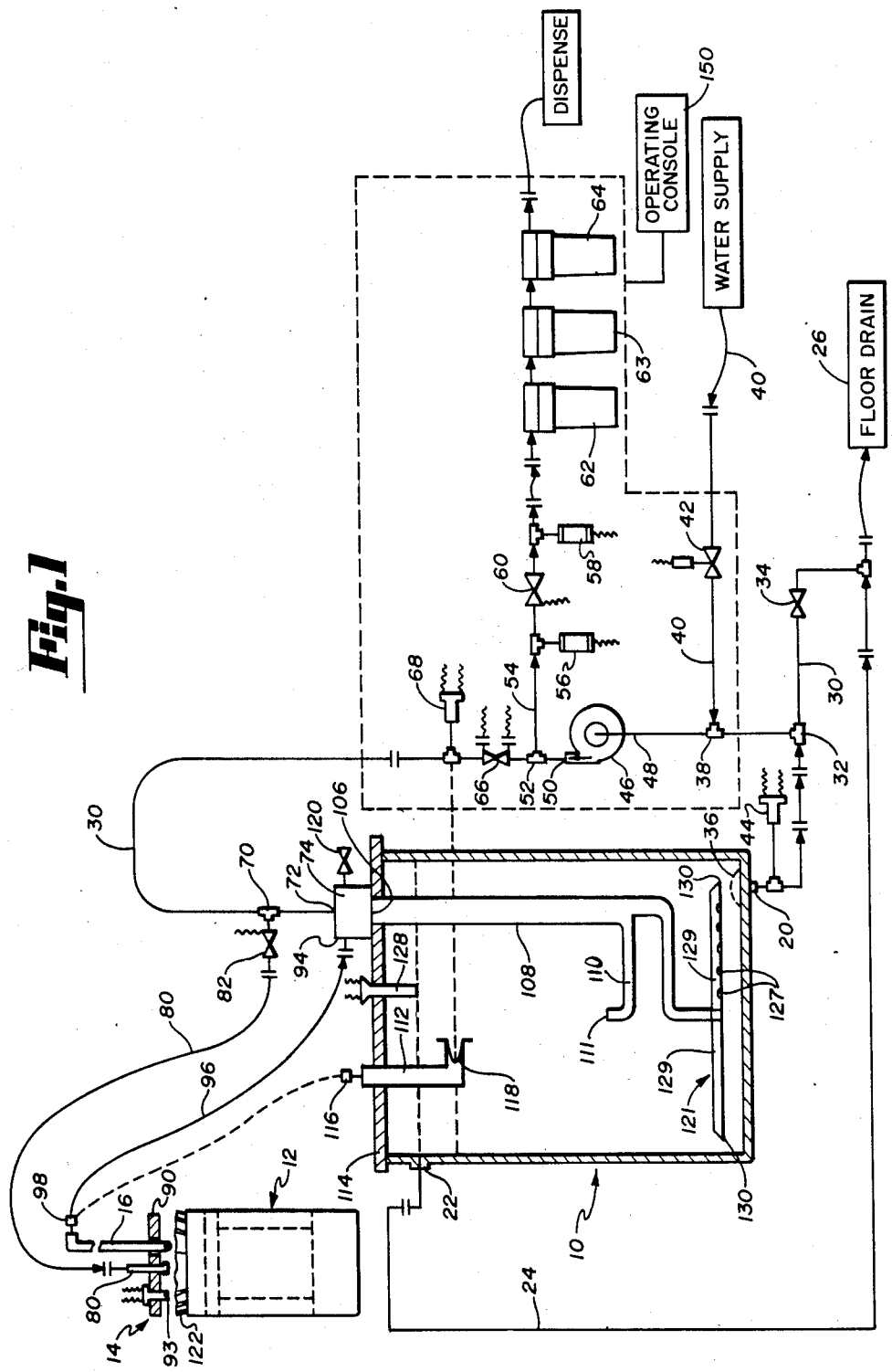
FIG. 1 is a schematic diagram of the dialysis solution mixing system according to the present invention.

The preferred embodiment of the dialysis concentrate solution mixing system of the present invention is depicted in FIG. 1. The system comprises a dialysis concentrate solution mix tank 10, a shipping container 12 specially prefilled with dry hemodialysis chemicals, a spray head assembly 14 and a suction pick up tube 16. Fluid connecting means join the tank spray head assembly and suction pick-up tube to the tank 10.

The mixing tank 10 may be a generally cylindrically shaped tank. The tank volume is dependent only on the user's desires. Preferably, the tank volume is selected to correspond to the volume needed to use the contents of a standard shipping drum of dry dialysis chemicals. A single drum in the preferred form of the invention contains all of the chemicals required to make a batch. This avoids the need for multiple packages containing different chemicals. It also eliminates the need to weigh out the quantity of each dry chemical needed. The possibility of operator error is thereby reduced.

Tank 10 includes a drain 20 which allows the tank to empty. An overflow drain 22 may be provided high on the tank walls and is connected by overflow line 24 to floor drain 26. Tank drain 20 is connected to a dialysis concentrate tank delivery line generally indicated as 30 and includes a Tee 32 and a drainage valve 34 that leads to floor drain 26. Tank drain 20 preferably includes a removable drain screen 36 to prevent large particles from entering line 30. The delivery line branches at Tee 38 to a water supply line 40 which includes water supply valve 42.

A level sensor 44 is provided in delivery line 30 beneath tank drain 20. Level sensor 44 may be of the ultrasonic type such as the air and foam detector described in U.S. Pat. No. 4,068,521 to Cosentino et al. All level sensors discussed throughout the specification may be the ultrasonic type discussed above.

Delivery line 30 branches at Tee 38 and leads to a pump 46 having an inlet port 48 and discharge port 50. Pump 46 may be a rotary displacement pump or any pump capable of handling salt solution or slurrys.

Delivery line 30 proceeds from pump 46 to Tee 52 where it splits and joins dialysis fluid delivery line 54. Dialysis fluid delivery line 54 includes a low pressure sensor 56, high pressure sensor 58, valve 60 and delivery line filters 62, 63 and 64. Dialysis delivery line 54 delivers prepared dialysis concentrate solution as concentrate to be diluted in conventional proportioning systems or for direct patient use, shown schematically as the dispensing box in FIG. 1. Conductivity of the solution and other parameters of the concentrate solution are desirably checked at this point before diluting the concentrate solution for patient treatment.

Delivery line 30 includes a delivery line valve 66 and a level sensor 68, which may be of the same type as level sensor 44 as shown in FIG. 1. Delivery line 30 branches at Tee 70 wherein one leg of the Tee proceeds to a pressure inlet port 72 of a jet pump 74 and the other leg of the Tee is connected to spray head line 80.

Figure 2:
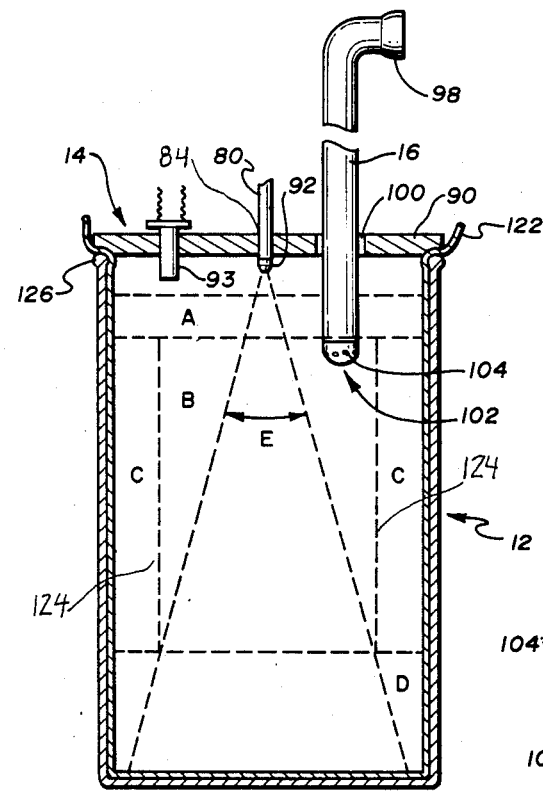
FIG. 2 is a partial sectional view of the spray head and chemical drum of FIG. 1.

Spray head line 80 includes a valve 82 and extends through the spray head assembly 14 as shown in FIG. 2.

Figure 3:
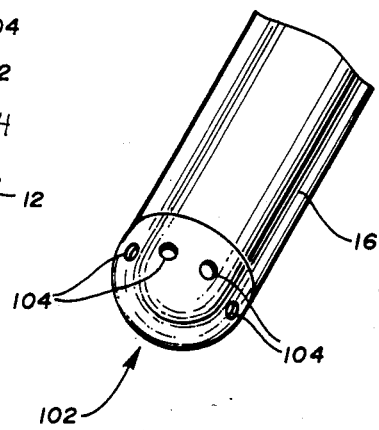
FIG. 3 is a fragmentary pictorial view of the pick-up wand plug of the invention.

Spray head assembly 14, as shown in FIGS. 1 through 3, includes a spray plate 90 which is constructed and arranged to conform to the opening of container 12 so as to form a splash shield. Preferably, spray plate 90 is formed from acrylic or similar corrosion-resistant material. Spray plate 90 rests on top of container 12 without descending therewithin.

Spray head line 80 is attached to and perforates spray plate 90 at inlet 84 as shown. Spray head line 80 terminates at the underside of spray plate 90 and includes a nozzle 92 which projects fluid passing through line 80 at a controlled spray angle. Preferably, nozzle 92 projects a full cone spray pattern having a relatively coarse spray over a narrow angle. A narrow spray angle results in high impact. A spray angle is selected which is narrow enough to be confined to the inner core region of container 12 which contains the chemicals such as sodium acetate which are solubilized and slurried more slowly. Preferably, a 15-20 degree spray angle is utilized. A suitable nozzle is a Fulljet ® brand nozzle available from Spraying Systems Company of Wheaton, Ill. under their designation 15150. Nozzles are preferably fabricated from polyvinyl chloride or other salt and corrosion resistant material.

The suction port 94 of jet pump 74 is connected to a flexible conduit 96 which in turn is connected to a hollow pick up tube 16 by means of a disconnect coupling 98. The wand is formed of a rigid, hollow suction tube. Wand or tube 16 is inserted through perforation 100 in spray plate 90 which is separated from the centrally located inlet 84. Wand 16 is of a length sufficient to contact the bottom of container 12 when inserted through perforation 100 of spray plate 90. The open suction end of wand 16 preferably includes a rounded plug 102 having a plurality of openings 104 therethrough. Openings 104 must be sized to prevent cloggage from the chemicals within the drum. It has been found that openings of a diameter of about one tenth of an inch in diameter or greater is sufficient. Wand 16 is merely allowed to gravity feed downwardly through perforation 100 in spray plate 90.

A level sensor 93 of the ultrasonic type referred to above may be provided as a component of the spray head assembly 14, as shown in FIG. 2. A signal from level sensor 93 could be used to automatically shut down fluid flow into container 12 if excess liquid is present in the container due to a clogged pickup tube 16 or the like.

Discharge port 106 of jet pump 74 is connected to supply pipe 108 which enters tank 10. Supply pipe 108 includes a branch pipe section 110 which includes a reduced diameter opening 111 which directs fluids upwardly in the tank as shown. The remaining fluid driven by jet pump 74 drives an impeller 121 near the bottom of tank 10. Impeller 121 may be any suitable fluid driven impeller such as the type having several arms extending from a central hub. Each arm 129 may include a plurality of perforations 127 spaced along the arm so as to project fluid downwardly at about a 45° angle from the horizontal plane defined by the arms. Preferably, each arm 129 includes a perforation 130 at its end, as shown, so as to project fluid downwardly and outwardly to the peripheral edge of the tank so as to provide flow at a region where stagnation will tend to occur.

The fluid coupling between pipe 108 and impeller 121 may be constructed in a manner similar to the coupling of impellers in conventional automatic dishwashers. A tight fluid connection is not necessary since leakage is not harmful and will merely decrease the efficiency of the impeller.

A second fixed suction pipe 112 penetrates tank top 114. Suction pipe 112 includes a coupling 116 which may be connected to flexible conduit 96 at coupling 98. Dotted line 99 in FIG. 1 represents the connection between line 96 and pipe 112. Suction pipe 112 may include an open mesh sock 118 at its lower end which serves to break up foam and to entrap foreign matter entering the pipe. Alternatively or additionally, mixing action within tank 10 may be supplied by mechanical stirring devices.

The addition of air into the solution entering tank 10 through supply pipe 108 increases the mixing action within tank 10. Air is ordinarily picked up through suction tube 16 during its operation. Pump 74 may be constructed with a second suction inlet controlled by a manual air bleeder valve or orifice 120. Air bleeder valve 120 may be adjusted to introduce air into line 108. The rate of suction from the drum exceeds the rate in which solution enters the drum through spray nozzle 92 to increase the mixing action.

Chemical Packaging

It has been found that sodium acetate is transferred from the drum and dissolves very slowly in water in comparison to sodium chloride, sodium bicarbonate, calcium chloride, magnesium chloride, potassium chloride and dextrose. Also, sodium acetate tends to chunk up and forms a hard, glassy, glazed appearance. Therfore, it has been found that if sodium acetate is added to a given quantity of water which already contains other hemodialysis chemicals, the sodium acetate will transfer slowly and go into solution slowly. Chunks of sodium acetate within a tank may continue to dissolve over a long period of time continually changing the concentration of sodium acetate within the mixed tank.

Although it would be possible to add the sodium acetate required for a batch of hemodialysis concentrate solution from a separate container before the other chemicals were added, it is preferable to have all the dry chemicals to be used in one container. The use of several containers of dry chemicals greatly increases the risk of operator error in locating the correct drums, weighing out the correct amounts and the like. However, as explained above, it has been found that a simple mixture of dry hemodialysis chemicals within a single container leads to a very long dialysis concentrate solution preparation time.

The inventors have found that if problem chemicals having poor transfer characteristics such as sodium acetate are loaded into an inner core region of the drum or container that diluent may be concentrated within within this inner core using the system described above in order to aid dissolution and slurrying of the problem chemical. Container 12 is shown in FIG. 2 and may be a standard fiber drum having a protective liner 122 therewithin. The drum may be loaded with hemodialysis chemicals in many layers. As shown, a first lower layer D may be laid at the bottom of the drum. A core mold or sleeve having cylindrical upstanding walls or other suitably shaped walls is then centered within the drum. The core mold would be positioned between regions C and B at the interface of the regions shown by dotted lines in FIG. 2. Hemodialysis chemicals which are relatively easily dissolved and slurried may be placed in the region marked as C in FIG. 2. The inner core B is filled with the sodium acetate or other dry chemical which slurries and/or dissolves slowly or poorly. The sleeve is then removed. A final layer of dry chemicals labeled as A in FIG. 2 may then be added across the top of the container.

EXAMPLE

The fiber drum having an outside diameter of 20½ inches and 43 inches in height is filled with a mixture of approximately 442 pounds of chemicals. The drum contains about 233 pounds of NaCl, 109 pounds of $Ch_3COONa$, 835 pounds of dextrose, 5.8 pounds of $MgCl_2$, 9.75 pounds of $CaCl_2.H_2O$ and 8.5 pounds of KCl. Sodium chloride is loaded into lower region marked D in FIG. 2. Dextrose is added to the $CaCl_2.H_2O$ outer periphery marked C separated by sleeve 124 from the inner core. Sodium acetate is then added to form the inner core identified as B. Sleeve 124 is removed and magnesium chloride, potassium chloride and calcium chloride are added to the top of the drum. In this example, the core sleeve had an inside diameter of 15½ inches and a height of 30½ inches. Of course, diameters and heights are merely dependent on the size container chosen and the total amount of chemicals involved.

Tank 10 is charge with USP purified water standard hemodialysis quality water by opening valve 42. Water fills the tank to a predetermined level which may be indicated by an electrical level sensor 68 whose signal causes the solenoid on valve 42 to shut off the water flow. In this example 100 gallons of water is metered into the tank. Level sensor 68 will also protect pump 46 from running when no liquid is available. The signal from level sensor 68 may be used to turn off power.

Preferably, the tank is prefilled with less than the required volume of water during transfer of the dry chemicals. After all the chemicals have been transferred additional water is added to bring total volume of mixing tank 10 to the predetermined level desired for proper concentrate composition. After the chemicals are fully dissolved, additional water is added if necessary to bring the total volume to the proper level.

After all the chemicals have been added and mixed, the remaining water is then added and mixed in a manner not unlike using a volumetric flask.

An operator then positions the spray head assembly 14 over rim 126 of the opened, prefilled dry chemical container. The protective liner 122 of the drum is preferably pulled upwardly as shown in the figures to provide additional splash protection. Wand 16 is inserted through perforation 100 in spray plate 90 until it contacts the dry chemicals within the container. Spray plate 90 may simply rest on top of rim 126 or it may be configured in a manner similar to a drum lid so as to provide a better seal.

Delivery line valve 66 and spray head valve 82 are opened and pump 46 is turned on. Water enters spray head assembly 14 and is sprayed through nozzle 92 at a rate of about 9 gallons per minute. The 15°-20° spray angle formed by the nozzle is shown in FIG. 2 by dotted lines and its area of impact is marked as region E. In this example, some of the dry chemicals within region A are immediately slurried and dissolved. The underlying sodium acetate is then slurried and solubilized forming a generally cone shaped void within the inner core which contains the sodium acetate. As the process continues, the overhanging walls of the sodium acetate tend to fall inwardly where the sodium acetate chunks are again contacted by the high velocity course spray from nozzle 92. Removal of the chemicals within the drum proceeds relatively slowly at first and reaches a maximum rate of about 30 pounds per minute. The suction rate of slurried chemicals out of the drum is about 13 gallons per minute.

By the time the spray from nozzle 92 contacts sodium chloride within region D nearly all of the sodium acetate has been slurried, solubilized and transported to tank 10. The remaining chemicals within the drum are easily solubilized and are carried over to drum 10 through wand 16 for further mixing.

The air and slurry of chemicals are carried into tank 10 through supply pipe 108. The direction of pipe section 110 tends to create a swirling action within the tank to improve the mixing. The amount of air entering tank 10 may be adjusted through the use of air bleeder valve 120 or by adjusting the flow of liquid to the spray head. The process continues, with solution from tank 10 continuously replacing the solution and chemicals removed from the drum by wand 16. Eventually, all the chemicals are removed from the drum. At this time, valve 82 is closed and wand 16 empties the drum.

Impeller 121 driven by jet pump 74 drives fluid against the bottom and lower sides of mix tank 10 throughout the process.

The level of chemicals and water within tank 10 has now reached about 130 gallons. Pick up wand 16 is disconnected from flexible conduit 96. Conduit 96 is then connected to coupling 116 of suction pipe 112. The fluid within tank 10 is pulled through suction pipe 112 and cycled back through supply pipe 108. The normal foam which tends to build up in the tank during mixing is broken up when it passes through open mesh sock strainer 118.

Tank 10 is then filled to its final volume with additional water. The tank is filled until it reaches level sensor 128 whose signal causes valve 42 to close. The dialysis solution within the tank is then mixed.

After thoroughly mixing, the dialysis concentrate solution leaves tank 10 through delivery line 30 and is filtered prior to use. The conductivity of the dialysis concentrate solution is then checked with the meter such as the RS-2120 dialysis concentrate solution meter from Renal Systems, Inc. of Minneapolis, Minn. Preferably a gang of delivery line filters 62 through 64 is employed to remove successively smaller contaminants. A high pressure sensor 58 maybe used to monitor the condition of the filters. If the filters become clogged, the pressure rises and sensor 58 may send a signal to a controller 150 which may indicate the condition and/or shut the system down for filter replacement.

A low pressure sensor 56 is preferably provided to provide indication of suction conditions and the operation of pump 46. An operator may be alerted of insufficient pressure by a signal from low pressure sensor 56. The pump may then be shut off manually or automatically to prevent damage due to running without solution.

The dialysis concentrate solution mixing system and process may be operated manually or preferably automatically with the use of known controllers. Generally, all valves may be solenoid controlled, normally closed valves which open when energized from controller 150.

A suitable controller 150 may include a power switch, a circulation switch which causes the dialysis solution to cycle and mix prior to or during delivery and a dispensing switch. The dispensing switch may include an indicator light which indicates that tank 10 is empty when level sensor 44 senses air instead of fluid.

Operator mixing controls may include an on/off switch which initially fills tank 10 to the height indicated by level sensor 68 and then activates pump 46 and opens valve 66 and 82 when a second switch is depressed. Indicator lights may identify the stage of the process and automatic timers may control the mixing time.

A variety of system alarms may be included to indicate that the tank is full as sensed by level sensor 128, low pump pressure as indicated by pressure sensor 56 and the like.

All of the controls which automate the system may be readily added and custom tailored by those skilled in the art. The controllers per se do not form a part of this invention.

The unique prepackaged drums of dry chemicals, system and process of emptying the drum of the invention results in a reduction of processing time from about 2½ hours to about 45 minutes. Less oepator time is involved and the use of a single drum prevents errors which may result from weighing chemicals from several drums. Although the invention has been described with specific reference to placing sodium acetate within the inner core of the containers, the packaging may be altered so long as the most troublesome chemical to transfer is placed within an area which may be impacted by a relatively high velocity water spray which is directed so as to selectively contact that chemical. For example, the troublesome chemical having slow transfer characteristics could be loaded into a container along an outside edge, such that the container forms part of its boundary. A spray nozzle would then be selected and aimed so as to impact onto the chemical confined within such a region. However, the preferred packing arrangement includes the generally centrally located inner region and nozzle system described in the example.

It must also be remembered that the processes and systems of the invention are applicable to transferring any dry chemicals for mixing and is not limited to hemodialysis chemicals.

In considering this invention it should be remembered that the present disclosure is illustrative only and that the scope of the invention should be determined by the appended claims.

What is claimed is:

1. A prepackaged container of all of the dry chemicals needed to prepare an aqueous solution by introduction of water into said container, the prepackaged container including at least one chemical which when admixed with pure water less readily forms a solubilized mixture and slurry than other chemicals within the container, the prepackaged container consisting of:
   (a) a watertight container having a removable lid,
   (b) a plurality of dry chemicals within said container, and
   (c) said dry chemicals being positioned within said container such that a predetermined portion of said container consists essentially of only those chemicals which solubilize and form a slurry with pure water less readily than the other chemicals positioned within other portions of said container.

2. The prepackaged container of dry chemicals of claim 1 wherein said chemicals which form a solubilized mixture and slurry in pure water less readily than the other said chemicals are positioned within an inner core region of the container and said other chemicals surround said inner region.

3. A prepackaged container of dry hemodialysis chemicals for use in preparing hemodialysis solution by the addition of water to said container, the prepackaged container comprising:
   (a) a container;
   (b) a plurality of dry hemodialysis chemicals;
   (c) said hemodialysis chemicals being positioned within said container such that an inner core region of said container consists essentially of chemicals which form a solubilized mixture and slurry in pure water less readily than other chemicals within said container surrounding same.

4. A prepackaged container of dry hemodialysis chemicals for use in preparing hemodialysis solution by the addition of water to said container, the prepackaged container comprising:
   (a) a container;
   (b) dry hemodialysis chemicals selected from the group consisting of calcium chloride, magnesium chloride, potassium chloride, dextrose, sodium acetate, sodium bicarbonate and sodium chloride; and
   (c) said hemodialysis chemicals being positioned within said container such that an inner core region of said container is filled with sodium acetate, the remainder of said container being filled with the other chemicals.

5. A prepackaged container filled with hemodialysis chemicals for use in preparing hemodialysis solution from a water injection, suction removal system which injects water into said container and suctions the resulting solution out of said container, the prepackaged container comprising:
   (a) a container;
   (b) dry hemodialysis chemicals having differing solubilization and slurrying characteristics; and
   (c) said dry hemodialysis chemicals arranged within said container such that an inner core region of said container consists essentially of hemodialysis chemicals having the slowest slurrying and solubility characteristics in water.

6. A prepackaged container filled with hemodialysis chemicals for use in preparing hemodialysis solution employing a water injection dialysis solution mixing system which injects water into said container, the prepackaged container comprising:
   (a) a container;
   (b) at least two dry hemodialysis solution chemicals, at least one of which slurries and dissolves in water substantially more slowly than the other chemicals; and
   (c) said dry hemodialysis chemicals being arranged within said container such that an inner core region of said container consists essentially of the most slowly dissolving and slurrying chemicals, the remainder of said container being filled with such other hemodialysis chemicals.

7. A blending system for preparation of hemodialysis solution from water and dry chemicals comprising:
   (a) a dialysis solution tank;
   (b) means for supplying water into said tank;
   (c) a source of hemodialysis chemicals, said chemicals being arranged within said source such that only the chemicals having the slowest solubilization and slurry characteristics are positioned within an inner core region of said source and the other more soluble chemicals are positioned outside of the inner core region;
   (d) delivery means for conveying water and water-chemical diluent within said tank to said source of chemicals; said delivery means including a nozzle means for directing a high velocity spray of the tank liquid over a spray angle which is directed onto the inner core region of said source of chemicals so as to cause the chemicals therewithin the dissolve and form a slurry before the chemicals outside of the inner core region are substantially dissolved or slurried;
   (e) pick-up wand means for conveying said dissolved chemicals and slurry within said chemical source to said dialysis solution tank; and
   (f) dialysis concentrate solution tank mixing means for receiving said dissolved chemicals and slurry from said pick-up wand means for mixing same within said tank.

8. The blending system of claim 7 wherein said mixing means includes impeller means within and adjacent the bottom of said tank and being driven by fluid, said impeller means including an impeller having a plurality of radially extending arms extending from a central hub, said hub being rotatably mounted to a means supplying driven fluid, each of said arms including perforations constructed and arranged such that driven fluid passing therethrough causes said impeller to rotate.

9. The blending system of claim 8 wherein said impeller arm perforations are arranged along an edge of each arm so as to project driven fluid downwardly toward the bottom of said tank, said arms further including at least one perforation at the free ends, said perforation being arranged so as to project driven fluid outwardly and downwardly toward the edges of said tank bottom.

10. A method for preparing hemodialysis solution from a diluent of water and from dry chemicals comprising:
  (a) metering diluent into a dialysis solution tank;
  (b) loading a predetermined quantity of dry chemicals having the amount of chemicals required to make up the hemodialysis solution into a container, said container being loaded with dry chemicals which dissolve and form a slurry more slowly in pure water than the other chemicals within an inner core region about which the other chemicals are loaded;
  (c) conveying said diluent from said tank onto the chemicals within said inner core region of said container so as to substantially solubilize and disperse chemicals therewithin before the other chemicals within said container are dissolved and dispersed;
  (d) conveying the solubilized and dispersed chemicals from said container to said dialysis solution tank;
  (e) continuing said conveying of diluent from said tank to said container and said solubilized and dispersed chemicals to said dialysis solution tank until all of said chemicals have been conveyed to said tank; and
  (f) mixing said chemicals within said tank until a uniform concentration is obtained therewithin.

11. The method of claim 10 wherein said diluent from said dialysis solution tank is sprayed into said container in a spray pattern having a spray angle which directs diluent only into said inner core region.

12. The method of claim 10 wherein solubilized and dispersed chemicals within said container are conveyed from said container to said dialysis solution tank by suction through a pick-up wand.

13. The method of claim 10 wherein sodium acetate is loaded into said inner core region of said container and chemicals selected from the group consisting of sodium chloride, dextrose, potassium chloride, calcium chloride, lactic acid, sodium bicarbonate and magnesium chloride are loaded within the remaining regions within the container.

* * * * *

UNITED STATES PATENT AND TRADEMARK OFFICE
CERTIFICATE OF CORRECTION

PATENT NO. : 4,664,891
DATED : May 12, 1987
INVENTOR(S) : Louis C. Cosentino et al It is certified that error appears in the above-identified patent and that said Letters Patent is hereby corrected as shown below:

Column 2, line 2, delete "chlroide" and insert - chloride -

Column 8, line 66, delete "oepator" and insert - operator

Signed and Sealed this

First Day of September, 1987

Attest:

DONALD J. QUIGG

Attesting Officer

Commissioner of Patents and Trademarks